United States Patent
Okada et al.

(10) Patent No.: US 10,274,617 B2
(45) Date of Patent: *Apr. 30, 2019

(54) RADIOGRAPHIC IMAGING DEVICE AND RADIOGRAPHIC IMAGING METHOD USING INTERPOLATION FROM HEXAGONAL TO SQUARE PIXELS

(71) Applicant: FUJIFILM CORPORATION, Minato-ku, Tokyo (JP)

(72) Inventors: Yoshihiro Okada, Kanagawa (JP); Takao Kuwabara, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 1038 days.

This patent is subject to a terminal disclaimer.

(21) Appl. No.: 14/179,569

(22) Filed: Feb. 13, 2014

(65) Prior Publication Data

US 2014/0161230 A1    Jun. 12, 2014

Related U.S. Application Data

(63) Continuation of application No. PCT/JP2012/070375, filed on Aug. 9, 2012.

(30) Foreign Application Priority Data

Aug. 14, 2011 (JP) ................... 2011-177363

(51) Int. Cl.
*G01T 1/24* (2006.01)
*H04N 5/32* (2006.01)
(Continued)

(52) U.S. Cl.
CPC ............... *G01T 1/247* (2013.01); *H04N 5/32* (2013.01); *A61B 6/502* (2013.01); *H04N 5/23235* (2013.01)

(58) Field of Classification Search
None
See application file for complete search history.

(56) References Cited

U.S. PATENT DOCUMENTS

| 2003/0015664 A1 | 1/2003 | Agano | |
|---|---|---|---|
| 2009/0009637 A1* | 1/2009 | Wada | ..................... H04N 9/045 348/241 |

(Continued)

FOREIGN PATENT DOCUMENTS

| JP | 2000-244733 A | 9/2000 |
|---|---|---|
| JP | 2003-255049 A | 9/2003 |

(Continued)

OTHER PUBLICATIONS

Partial English language translation of the following: Office action dated Jun. 2, 2015, from the JPO in a Japanese patent application corresponding to the instant patent application.

(Continued)

*Primary Examiner* — J Choi
(74) *Attorney, Agent, or Firm* — Solaris Intellectual Property Group, PLLC

(57) ABSTRACT

A radiographic imaging device includes a radiation detection element including plural same sized hexagonal shaped pixels that detect radiation and are arrayed in a honeycomb pattern, and a pixel density conversion section that performs interpolation processing such that first image data obtained from the radiation detection element is converted into second image data representing an image in which plural pixels are arrayed in a square grid pattern, wherein when d1max denotes the length of the longest diagonal of the hexagonal shaped pixels, S1 denotes the surface area of the hexagonal shaped pixels, and d2max denotes the length of the diagonals of the square grid of the second image data, d1max is (Continued)

equal to or greater than d2max, and d2max is equal to or greater than the value of the square root of S1.

12 Claims, 9 Drawing Sheets

(51) Int. Cl.
*H04N 5/232* (2006.01)
*A61B 6/00* (2006.01)

(56) References Cited

U.S. PATENT DOCUMENTS

| | | |
|---|---|---|
| 2009/0032680 A1 | 2/2009 | Watanabe et al. |
| 2011/0199394 A1* | 8/2011 | Toraichi .................. G06T 3/403 345/671 |

FOREIGN PATENT DOCUMENTS

| | | | |
|---|---|---|---|
| JP | 2003255049 A | * | 9/2003 |
| JP | 2006-029839 A | | 2/2006 |
| JP | 2007-059887 A | | 3/2007 |
| JP | 2009-021988 A | | 1/2009 |
| JP | 2009-049562 A | | 3/2009 |

OTHER PUBLICATIONS

Extended European Search Report dated Mar. 3, 2015 from the EPO in an European patent application corresponding to the instant patent application.
Written Opinion of the ISA issued in International Application No. PCT/JP2012/070375 dated Sep. 18, 2012.
International Search Report issued in International Application No. PCT/JP2012/070375 dated Sep. 18, 2012.
Communication pursuant to Article 94(3) EPC dated Jan. 17, 2017, issued in corresponding EP Patent Application No. 12808217.9.

* cited by examiner

FIG.6

$\sqrt{S1} \leq d2max \leq d1max$     (1)

| REGULAR HEXAGONAL SHAPE | | | SQUARE AFTER CONVERSION | | | |
|---|---|---|---|---|---|---|
| S1 | PP1 (x) | d1max | S2 | PP2 | d2max | $\sqrt{S1}$ |
| 4489.5 | 72 | 83.1 | 2500 | 50 | 70.7 | 67.0 |

(2)

| S1 | PP1 (x) | d1max | S2 | PP2 | d2max | $\sqrt{S1}$ |
|---|---|---|---|---|---|---|
| 4243.5 | 70 | 80.8 | 4225 | 65 | 91.9 | 65.1 |
| 4243.5 | 70 | 80.8 | 3600 | 60 | 84.9 | 65.1 |
| 4243.5 | 70 | 80.8 | 3025 | 55 | 77.8 | 65.1 |
| 4243.5 | 70 | 80.8 | 2500 | 50 | 70.7 | 65.1 |
| 4243.5 | 70 | 80.8 | 2025 | 45 | 63.6 | 65.1 |

FIG.7

$d2max \leq d1max \leq \sqrt{(2 \times S1)}$     (1)

| SQUARE CORRESPONDING TO S1 | | | HEXAGONAL SHAPE | | | SQUARE AFTER CONVERSION (MINIMUM OUTPUT PIXEL SIZE) | | |
|---|---|---|---|---|---|---|---|---|
| S0 | PP0 | d0max | S1 | PP1 (x) | d1max | S2 | PP2 | d2max |
| 4871.4 | 69.8 | 98.7 | 4871.4 | 75 | 86.6 | 2500 | 50 | 70.7 |

S0 = S1 $\sqrt{S1}$    $\sqrt{(2 \times S1)}$ (2)

CASES OF FLATTENED HEXAGONAL SHAPES

| S0 | PP0 | d0max | S1 | PP1 (x) | d1 (y) | FLATTENING RATIO | d1max |
|---|---|---|---|---|---|---|---|
| 8660.3 | 93.1 | 131.6 | 8660.3 | 100 | 115.5 | 100% | 115.5 |
| 4950.0 | 70.4 | 99.5 | 4950.0 | 100 | 66.0 | 63% | 105.3 |
| 5625.0 | 75.0 | 106.1 | 5625.0 | 100 | 75.0 | 70% | 106.8 |

US 10,274,617 B2

RADIOGRAPHIC IMAGING DEVICE AND RADIOGRAPHIC IMAGING METHOD USING INTERPOLATION FROM HEXAGONAL TO SQUARE PIXELS

CROSS-REFERENCE TO RELATED APPLICATIONS

This application is a continuation application of International Application No. PCT/JP2012/070375, filed on Aug. 9, 2012, which is incorporated herein by reference, in its entirety. Further, this application claims priority from Japanese Patent Application No. 2011-177363, filed on Aug. 14, 2011, which is incorporated herein by reference, in its entirety.

BACKGROUND OF THE INVENTION

Field of the Invention

The present invention relates to a radiographic imaging device and radiographic imaging method that image radiographic images.

Description of the Related Art

In recent years, radiographic imaging devices using radiation detection elements such as flat panel detectors (FPDs), in which an X-ray sensitive layer is disposed on a thin-film transistor (TFT) active matrix substrate and which can directly convert X-ray information into digital data, have been put into practical use. FPDs have advantages compared to conventional imaging plates, such as the user being able to check images instantly and also being able to check moving images, and the use of flat panel detectors continues to spread at a rapid pace. Various types of radiation detection elements have been proposed, such as, for example, the direct-conversion-type, which directly converts radiation into charges using a semiconductor layer and stores the charges, and the indirect-conversion-type, which first converts radiation into light using a scintillator comprising CsI:Tl, GOS ($Gd_2O_2S$:Tb), or the like and then converts the light into charges using a semiconductor layer and stores the charges.

Radiation detection elements have, for example, plural scan lines and plural signal lines that are disposed intersecting one another and pixels that are disposed in a matrix in correspondence to the intersections between the scan lines and the signal lines. The plural scan lines and the plural signal lines are connected to external circuits (e.g., amplifier integrated circuits (ICs) and gate ICs) at the peripheral portions of the radiation detection element.

In order to increase the resolution of FPDs, reducing the size of the pixels of the radiation detection element is effective. Particularly in direct-conversion-type radiation detection elements utilizing Se or the like, pixel size directly contributes to an improvement in resolution, so various types of radiation detection elements that improve picture quality by increasing definition have been proposed. For example, in FPDs for mammography, that has an emphasis on resolution, products with a small pixel size have been proposed.

However, in a case where the pixel size has been reduced, the quantity of charges that can be collected in proportion thereto decreases and, as a result, sensitivity (S/N) drops. For this reason, even if the resolution improves, this ends up causing the problem that the overall image quality detective quantum efficiency (DQE; which is proportional to {S/N× 1/resolution}) drops.

Meanwhile, in order to realize a balance between resolution and improving sensitivity, a detection device in which pixels are arranged offset by half a pitch in the X and Y directions and which performs inter-pixel interpolation processing on the basis of generated image information has been proposed (see Japanese Patent Application Laid-Open (JP-A) No. 2003-255049). Further, an X-ray detection device that uses hexagonal shaped pixels to improve the efficiency with which light is utilized has been proposed (e.g., see JP-A No. 2006-29839).

For example, a length (maximum diagonal length) d1max of the longest diagonal of a regular hexagonal shape and an surface area S1 of the regular hexagonal shape have the following relationship.

$$d1max = \sqrt{(8/3\sqrt{3}) \times S1} \approx \sqrt{1.54 \times S1}$$

In a case where the surface area S1 of the rectangular hexagon=10,000 $\mu m^2$, a comparison between a regular hexagonal pixel and a square pixel that have the same pixel area shows the following (see also FIG. 8A and FIG. 8B).

Square: length a1 of one side=100 $\mu m$, surface area S1=10,000 $\mu m^2$, maximum diagonal length d1max=141 $\mu m$ Regular hexagonal shape: length a1 of one side=107 $\mu m$; surface area S1=10,000 $\mu m^2$; maximum diagonal length d1max=123.5 $\mu m$ Consequently, given the same pixel area, the diagonal length d1max can be reduced by 12% in the case of the regular hexagonal shape compared to the square.

A radiographic image detected using the detection devices described in JP-A No. 2003-255049 and JP-A No. 2006-29839, which use hexagonal shaped pixels, becomes an image in which the pixels are arrayed in a honeycomb pattern. Meanwhile, many output devices such as printers and monitors are configured with the assumption that they will handle images in which the pixels are arrayed in a square grid pattern. For this reason, in order to make the detected radiographic image compatible with these output devices, it is necessary to perform pixel density conversion by performing interpolation processing on the detected radiographic image.

However, depending, for example, on the resolution (resolution) of the radiation detection element and the square grid image one wants to eventually obtain, the pixel information detected by the radiation detection element becomes wasted when the pixel density conversion has been performed. Further, for example, if the resolution after the pixel density conversion is too high compared to the resolution of the radiation detection element, the size of the image data after the conversion increases needlessly and processing speed drops.

The present invention provides a radiation detection element that may prevent an enlargement of the size of image data after pixel density conversion while improving resolution, a method of forming a radiation detection element, a radiographic imaging device using the radiation detection element, a radiographic imaging system, a radiographic imaging method, and a pixel density conversion method.

SUMMARY OF THE INVENTION

A first aspect of the present is a radiographic imaging device including: a radiation detection element, the radiation detection element including plural same sized hexagonal shaped pixels that detect radiation and are arrayed in a honeycomb pattern; and a pixel density conversion section that performs interpolation processing such that first image data obtained from the radiation detection element is converted into second image data representing an image in which plural pixels are arrayed in a square grid pattern, wherein, in the radiographic imaging device, following Formula (1) is satisfied, $$\sqrt{S1} \le d2max \le d1max \qquad \text{Formula (1)}$$

wherein d1max denotes the length of the longest diagonal of the hexagonal shaped pixels, S1 denotes the surface area of the hexagonal shaped pixels, and d2max denotes the length of the diagonals of the square grid of the second image data.

The condition of the latter half "d2max≤d1max" of Formula (1) means that the maximum diagonal length of the hexagonal shaped pixels before the pixel density conversion is equal to or greater than the diagonal length of the square grid after the pixel density conversion. By satisfying this condition, in the first aspect of the present invention, the resolution after the conversion becomes equal to or greater than the resolution before the conversion across all directions, and the signals of the pixels detected by the radiation detection element can be prevented from ending up being thrown out (wasted). Further, the condition of the former half "$\sqrt{S1} \le d2max$" of Formula (1) means that the diagonal length of the square grid of the image after the pixel density conversion is equal to or greater than the length of one side of a square grid having an surface area equal to the surface area S1 of the hexagonal shaped pixels before the pixel density conversion.

Here, d2max denotes the array pitch (maximum pitch) in the direction in which the resolution becomes the lowest among all directions in the pixel array after the conversion. Further, $\sqrt{(S1)}$ denotes the array pitch (minimum pitch) in the direction in which the resolution becomes the highest in a square grid having the same surface area as the hexagonal shaped pixels before the conversion in the radiation detection element. That is, the radiographic imaging device of the first aspect of the present invention uses hexagonal shaped pixels instead of square-shaped pixels to detect the radiographic image and performs pixel density correction, so that a sufficient sensitivity is obtained with the resolution one eventually wants to obtain for the place one originally wants to detect with square-shaped pixels. For this reason, in the first aspect of the present invention, it is not necessary to make the resolution after the pixel density conversion higher than the resolution of the square grid one originally wants to obtain. That is, it is not necessary to make the maximum pitch d2max of the square grid after the pixel density conversion smaller than the minimum pitch $\sqrt{(S1)}$ of a square grid having an area that is the same as the surface area S1 of the hexagonal shaped pixels used in order to obtain the resolution one originally wants to obtain. Even if d2max is made smaller than $\sqrt{(S1)}$, the size of the second image data after the conversion would increase needlessly, bringing about a drop in processing speed.

Consequently, by satisfying the condition of the former half of Formula (1), the first aspect of the present invention may prevent the size of the second image data after the conversion from becoming too large and may prevent a drop in processing speed.

A second aspect of the present invention, in the above first aspect, the following Formula (2) may also be satisfied.

$$d2max \le d1max \le \sqrt{(2 \times S1)} \qquad \text{Formula (2)}$$

The condition of the former half "d2max≤d1max" of Formula (2) is the same as the latter half of Formula (1). Consequently, in the second aspect of the present invention, by satisfying this condition, the resolution after the conversion becomes equal to or greater than the resolution before the conversion across all directions, and the signals of the pixels detected by the radiation detection element can be prevented from ending up being thrown out (wasted).

Further, the condition of the latter half "d1max≤$\sqrt{(2 \times S1)}$" means that the maximum diagonal length of the hexagonal shaped pixels before the pixel density conversion is equal to or less than the diagonal length of a square having an surface area that is equal to the surface area S1 of the hexagonal shaped pixels. That is, d1max denotes the array pitch (maximum pitch) in the direction in which the resolution becomes the lowest among all directions in the pixel array before the conversion. However, although resolution is increased by using hexagonal shaped pixels rather than square-shaped pixels, when d1max becomes larger than the diagonal length $\sqrt{(2 \times S1)}$ of a square having the same surface area S1 as the hexagonal shaped pixels, the resolution becomes lower than when using square-shaped pixels whose surface area is the same. For this reason, the effect of the hexagonal shape is not sufficiently obtained.

Consequently, the second aspect of the present invention can achieve a balance between the resolution and improving sensitivity by configuring the radiographic imaging device in such a way that d1max, d2max, and S1 satisfy Formula (2),.

Further, a third aspect of the present invention, in the above first or second aspect, the hexagonal shaped pixels may be formed to have a regular hexagonal shapeal shape.

A fourth aspect of the present invention, in the above aspects, the pixel density conversion section may perform the interpolation processing first out of a horizontal direction and a vertical direction in the first image data that has a shorter pixel array pitch and then may perform the interpolation processing in the other direction.

Further, a fifth aspect of the present invention, in the above aspects, may further include: a radiation source that applies radiation; and an image output device that outputs an image on the basis of the second image data.

A sixth aspect of the present invention is a radiographic imaging method, the radiographic imaging method including: detecting first image data using a radiation detection element that includes plural same sized hexagonal shaped pixels that detect radiation and are arrayed in a honeycomb pattern; and performing interpolation processing such that the first image data in converted to second image data representing an image in which plural pixels are arrayed in a square grid pattern, wherein in the radiographic imaging method, the following Formula (1) is satisfied, $$\sqrt{S1} \le d2max \le d1max \qquad (1)$$

wherein d1max denotes the length of the longest diagonal of the hexagonal shaped pixels, S1 denotes the surface area of the hexagonal shaped pixels, and d2max denotes the length of the diagonals of the square grid of the second image data.

Further, a seventh aspect of the present invention, in the above sixth aspect, the following Formula (2) may also be satisfied.

$$d2max \le d1max \le \sqrt{(2 \times S1)} \qquad \text{Formula (2)}$$

Further, an eighth aspect of the present invention, in the above sixth or seventh aspect, the hexagonal shaped pixels may have a regular hexagonal shape.

Further, a ninth aspect of the present invention, in the above sixth to eighth aspects, the interpolation processing may be first performed in the direction out of a horizontal direction and a vertical direction in the first image data that has shorter pixel array pitch, and then may perform the interpolation processing in the other direction.

A tenth aspect of the present invention, in the above sixth to ninth aspects, the method may further comprise outputting an image based on the second image data.

In this way, according to the above-described aspects of the present invention, there may be provided a radiation detection element, a method of forming a radiation detection element, a radiographic imaging device using the radiation detection element, a radiographic imaging system, a radiographic imaging method, and a pixel density conversion method, all of which may prevent an enlargement of the size of image data after pixel density conversion while improving resolution.

BRIEF DESCRIPTION OF DRAWINGS

Detailed explanation follows regarding exemplary embodiments of the present invention, with reference to the following drawings.

FIG. 6 is tables showing a specific example of verification results using Formula (1) according to the exemplary embodiment;

FIG. 7 is tables showing a specific example of verification results using Formula (2) according to the exemplary embodiment;

DETAILED DESCRIPTION OF THE INVENTION

A mode for carrying out the present invention will be described below with reference to the drawings. A case where the present invention is applied to a direct-conversion-type radiation detection element that directly converts radiation into charges will be described below.

Figure 1:
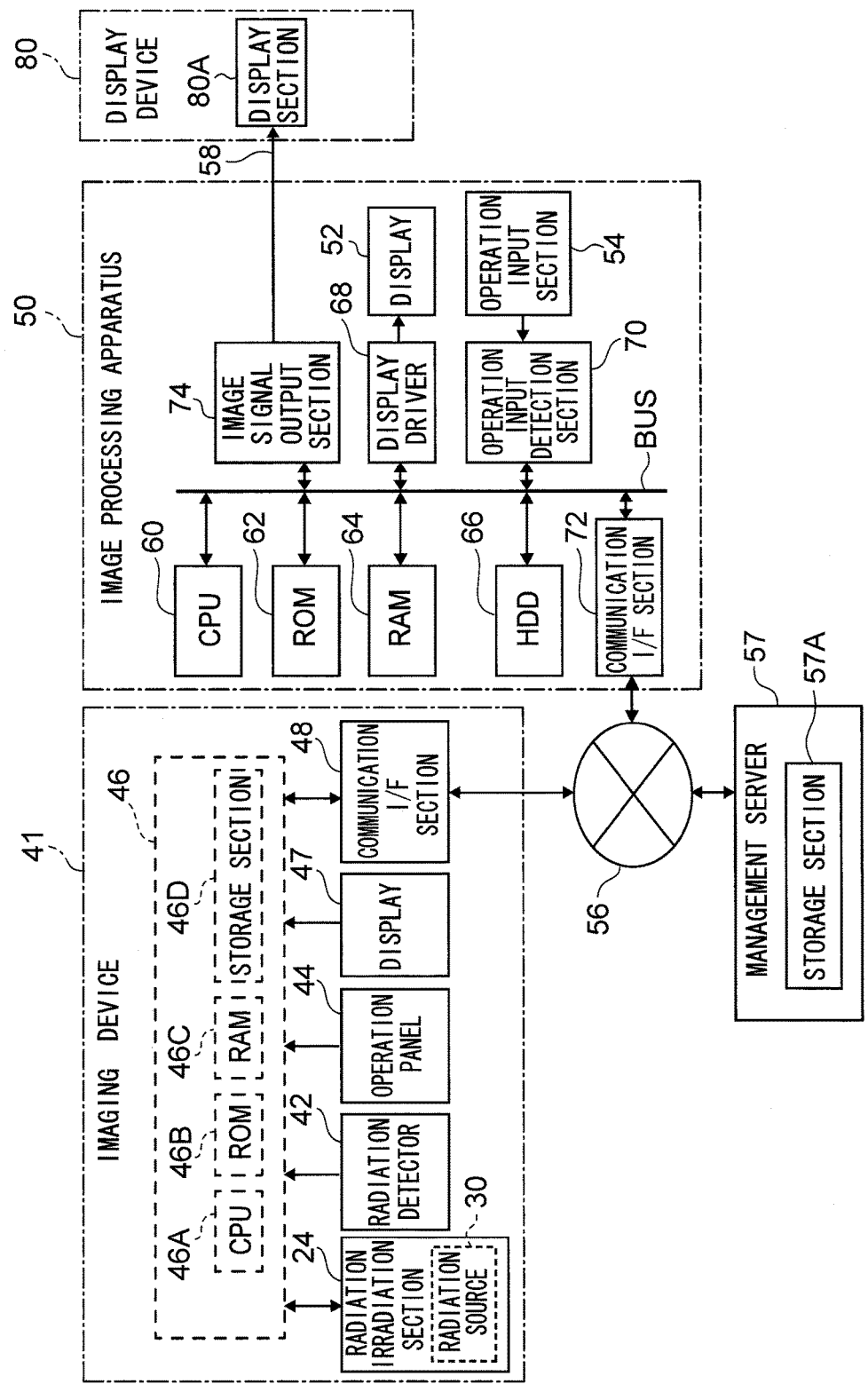
FIG. 1 is a configuration diagram showing the configuration of a radiation imaging system according to an exemplary embodiment.

FIG. 1 is a block diagram showing the configuration of a radiographic imaging system 100 according to the present exemplary embodiment. The radiographic imaging system 100 is equipped with an imaging device 41, an image processing apparatus 50, and a display device 80. The imaging device 41 images a radiographic image. The image processing apparatus 50 performs image processing on the image data representing the imaged radiographic image. The display device 80 displays subject images that the image-processed image data represent.

The imaging device 41 is equipped with a radiation detector 42, an operation panel 44, an imaging device control section 46, a display 47, and a communication I/F section 48. The radiation detector 42 is equipped with a radiation detection element 10 (see also FIG. 2) that detects a radiographic image. Imaging conditions, various types of operation information, and various types of operation instructions are input to the operation panel 44. The display 47 displays the imaging device control section 46 that controls the operation of the entire device and operation menus and various types of information. The communication I/F section 48 is connected to a network 56 such as a LAN and transmits and receives various types of information to and from other devices connected to the network 56.

The imaging device control section 46 is equipped with a CPU 46A, a ROM 46B, a RAM 46C, and a nonvolatile storage section 46D comprising an HDD, a flash memory, or the like and is connected to a radiation irradiation section 24, the radiation detector 42, the operation panel 44, the display 47, and the communication I/F section 48. In the storage section 46D, programs and so forth that the CPU 46A executes are stored. In the storage section 46D, the image data etc. representing the radiographic image are stored. For example, in a case where the imaging device 41 according to the present exemplary embodiment is used for mammography, radiographic image data obtained by imaging the breasts of a subject are stored in the storage section 46D.

The radiation detector 42 outputs image data representing a radiographic image to the imaging device control section 46 when radiation is applied to the radiation detector 42. The detailed configuration of the radiation detector 42 will be described later.

The imaging device control section 46 is capable of communicating with the image processing apparatus 50 via the communication I/F section 48 and the network 56 and transmits and receives various types of information to and from the image processing apparatus 50.

A management server 57 is further connected to the network 56. The management server 57 is configured to include a storage section 57A. The imaging device control section 46 is capable of communicating with the management server 57 via the communication I/F section 48 and the network 58.

The image processing apparatus 50 is configured as a server computer. The image processing apparatus 50 is equipped with a display 52, which displays operation menus and various types of information, and an operation input section 54, which is configured to include plural keys and to which various types of information and operation instructions are input.

Further, the image processing apparatus 50 is equipped with a CPU 60, a ROM 62, a RAM 64, an HDD 66, a display driver 68, an operation input detection section 70, a communication I/F section 72, and an image signal output section 74. The CPU 60 controls the operation of the entire device. In the ROM 62, various types of programs including a control program are stored beforehand. The RAM 64 temporarily stores various types of data. The HDD 66 stores and retains various types of data. The display driver 68 controls the display of various types of information on the display 52. The operation input detection section 70 detects states of operation with respect to the operation input section 54. The communication I/F section 72 is connected to the imaging device 41 via the network 56 and transmits and receives various types of information to and from the imaging device 41. The image signal output section 74 outputs image data to the display device 80 via a display cable 58. The image processing apparatus 50 acquires the image data representing the radiographic image from the imaging device 41 via the communication I/F section 72.

The CPU 60, the ROM 62, the RAM 64, the HDD 66, the display driver 68, the operation input detection section 70, the communication I/F section 72, and the image signal output section 74 are connected to one another via a system BUS. Consequently, the CPU 60 can access the ROM 62, the RAM 64, and the HDD 66. Further, the CPU 60 can control the display of various types of information on the display 52 via the display driver 68, control the transmission and reception of various types of information to and from the imaging device 41 via the communication I/F section 72, and control the images displayed on the display device 80 via the image signal output section 74. Moreover, the CPU 60 can grasp states of operation by a user with respect to the operation input section 54 via the operation input detection section 70.

In the image processing apparatus 50, later-described pixel density conversion is performed on the image data representing the radiographic image detected by the radiation detector 42. A program for performing this pixel density conversion is stored in the ROM 62 or the HDD 66. The image data output to the display device 80 become image data after pixel density conversion.

Figure 2:
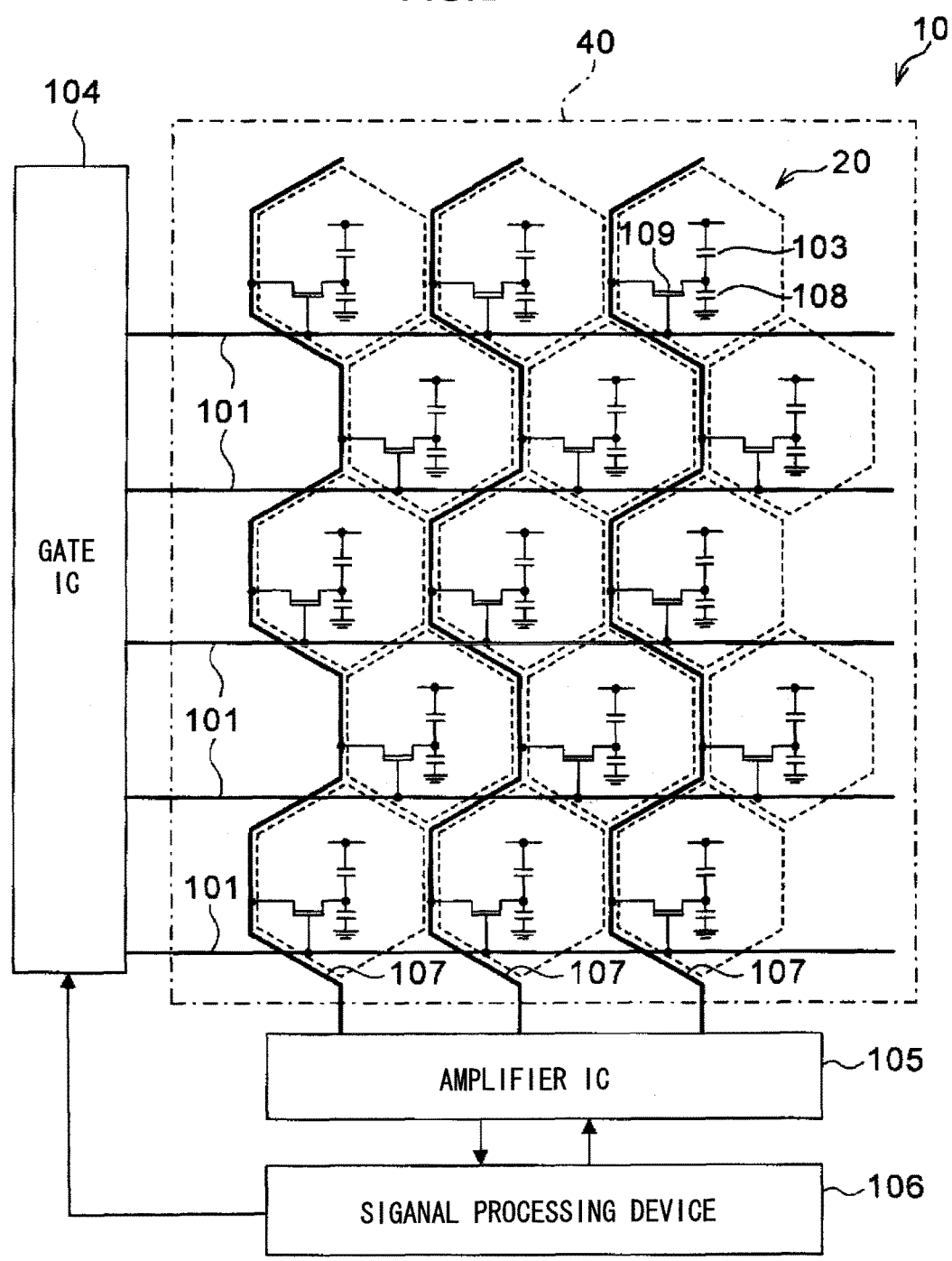
FIG. 2 is a configuration diagram showing the electrical configuration of a radiation detector including a radiation detection element according to the exemplary embodiment.

FIG. 2 shows the electrical configuration of the radiation detector 42 using the radiation detection element 10 according to the present exemplary embodiment.

The radiation detection element 10 is disposed with a rectangular detection region 40 and detects radiation applied to the detection region 40. Plural hexagonal shaped pixels 20 of the same size are adjacently arranged in the detection region 40. The hexagonal shaped pixels may have a regular hexagonal shape or a flattened hexagonal shape. The hexagonal shaped pixels also include substantially hexagonal shaped pixels in which each of the corner portions of the hexagon has been removed. Further, the hexagonal shaped pixels 20 include not only pixels with a shape such as the regular hexagonal shape or the flattened substantially hexagonal shape described above, but also parallel-hexagonal pixels in which the three sets of opposite sides are parallel and all of the internal angles are equal to or less than 180°. A "regular hexagonal shape" indicates a hexagon in which the lengths of the six sides are completely equal, but in actuality design limitations and manufacturing errors occur, so in consideration of those also, a substantially regular hexagonal shape is also included.

In the present exemplary embodiment, "hexagonal shaped pixels 20" indicates substantially hexagonal regions formed by signal lines 107 in FIG. 2, but it suffices for the pixels 20 to be arranged in a honeycomb pattern, and the shape of the pixels 20 is not limited to a substantially hexagonal shape. Further, for example, the hexagonal shaped pixels 20 may also be such that regions in which shapes having the same area and the same shape including later-described lower electrodes 11 (see FIG. 4) are arranged (that is, plane tessellation: gapless tiling) in a honeycomb pattern and divided are defined as single pixels. Further, the hexagonal shaped pixels 20 may also be such that regions in which shapes having the same area and the same shape including later-described TFT switches 109 (see FIG. 2) instead of the lower electrodes 11 are arranged in a honeycomb pattern and divided are defined as single pixels. Moreover, the hexagonal shaped pixels 20 may also be such that regions in which shapes having the same area and the same shape including at least one of not only the lower electrodes 11 and the TFT switches 109 but also later-described charge storing capacitors 108 or the like are arranged in a honeycomb pattern and divided are defined as single pixels.

In order to prevent complication of the pixel density conversion processing, it is preferred that the shape of the hexagonal shaped pixels 20 be such that the direction of one axis of the diagonals of the hexagon coincides with the direction of any one axis of a square grid after conversion and that the shapes divided by the axis be symmetrical with respect to the axis. That is, for example, referring to FIG. 5, a diagonal $d1(y)$ of the hexagon coincides with the direction of an axis of the square grid, and the two shapes divided by $d1(y)$ are symmetrical about $d1(y)$.

Figure 3:
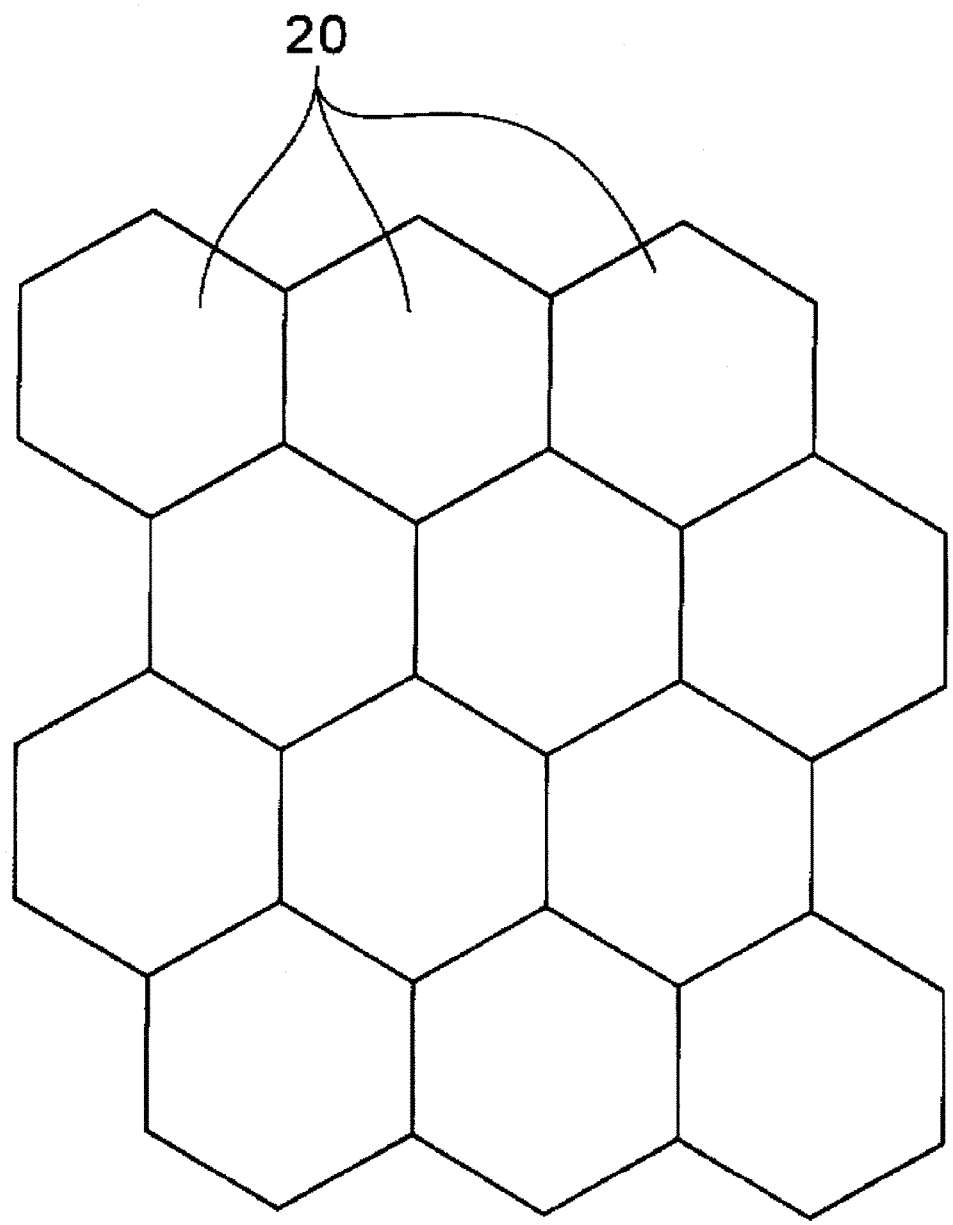
FIG. 3 is a plan view showing the state of an array of pixels in the radiation detection element according to the exemplary embodiment.

In the present exemplary embodiment, as shown in FIG. 3, the pixels 20 are arranged in a honeycomb pattern. Because of this, in the radiation detection element 10 according to the present exemplary embodiment, first pixel columns, in which plural hexagonal shaped pixels 20 of the same size are arrayed in a predetermined direction, and second pixel columns, in which plural hexagonal shaped pixels 20 of the same size as the pixels 20 in the first pixel columns are arrayed in the predetermined direction, and alternately arrayed in a direction intersecting the predetermined direction. In addition, in the radiation detection element 10 according to the present exemplary embodiment, the pixels 20 in the second pixel columns are arranged in correspondence to spaces between adjacent pixels in the first pixel columns, so the pixels 20 in the second pixel columns are arranged in such a way as to be offset by ½ of the array pitch of the pixels 20 in the first pixel columns. Further, the arrangement of the honeycomb pattern can also be described as follows in a case where it is seen from the row direction. First pixel rows, in which plural hexagonal shaped pixels 20 of the same size are arrayed in a predetermined direction, and second pixel rows, in which plural hexagonal shaped pixels of the same size as the pixels 20 in the first pixel rows are arrayed in the predetermined direction, are alternately arrayed in a direction intersecting the predetermined direction. In addition, the pixels 20 in the second pixel rows are arranged in correspondence to spaces between adjacent pixels in the first pixel rows, so the pixels 20 in the second pixel rows are arranged in such a way as to be offset by ½ of the array pitch of the pixels 20 in the first pixel rows.

In the case of imaging the breast of a subject, the hexagonal shaped pixels may also be formed flattened, with the breast being positioned and imaged in such a way that the short-width sides of the pixels are along the direction heading from the chest wall side toward the tip of the breast.

Here, a specific example will be provided and described. In the case of giving the pixels a flattened hexagonal shape, the pixels are squashed and flattened in the up-and-down direction of the page in FIG. 2 (the same is also true in FIG. 3 and in later-described (1) of FIG. 5). Because of this, the configuration becomes suited to a mammography machine that performs imaging with the chest wall corresponding to the upper portion of the page in FIG. 2. This is because in the case of a mammography machine, there is the need to image in high definition the depth direction from the chest wall side to the tip of the breast. Consequently, by giving the radiation detection element 10 a configuration where the pixels are crushed in this direction (that is, in such a way that the length of the hexagonal shaped pixels in the depth direction from the chest wall side to the tip of the breast becomes shorter than the width of the hexagonal shaped pixels in the direction intersecting that direction) and flattened and where external circuits such as gate ICs and amplifier ICs are not disposed on the chest wall side, the depth direction from the chest wall side to the tip of the breast can be imaged with full utilization of the available resolution.

Further, in the case of flattening the hexagonal shaped pixels, it is more preferred to make one diagonal of the three diagonals passing through the center of each pixel shorter than the other two diagonals and flatten the hexagonal shaped pixels in such a way that the other two diagonals have equal lengths (called a second flattening method) than to make one diagonal longer than the other two diagonals and flatten the hexagonal shaped pixels in such a way that the other two diagonals have equal lengths (called a first flattening method). Specifically, for example, taking (1) of FIG. 5 as an example, it is preferred to flatten the hexagonal shaped pixels in such a way that the diagonal length d1(y) in the up-and-down direction of the page becomes shorter than the other two diagonal lengths d1(x) (that is, to crush the hexagonal shaped pixels in the up-and-down direction of the page).

Figure 5:
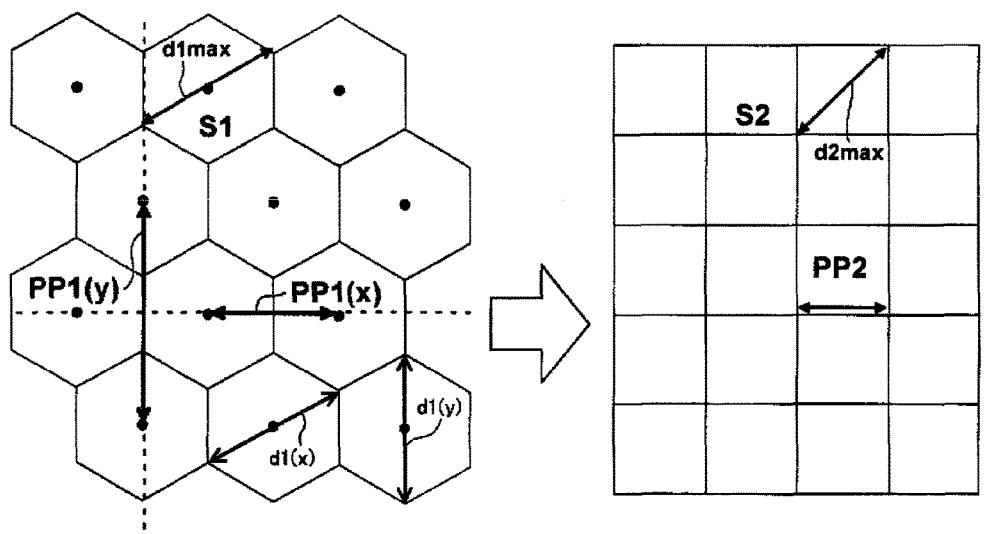
FIG. 5 is an explanatory diagram schematically explaining pixel density conversion of a radiographic image detected by the radiation detection element according to the exemplary embodiment.
Figure 8A:
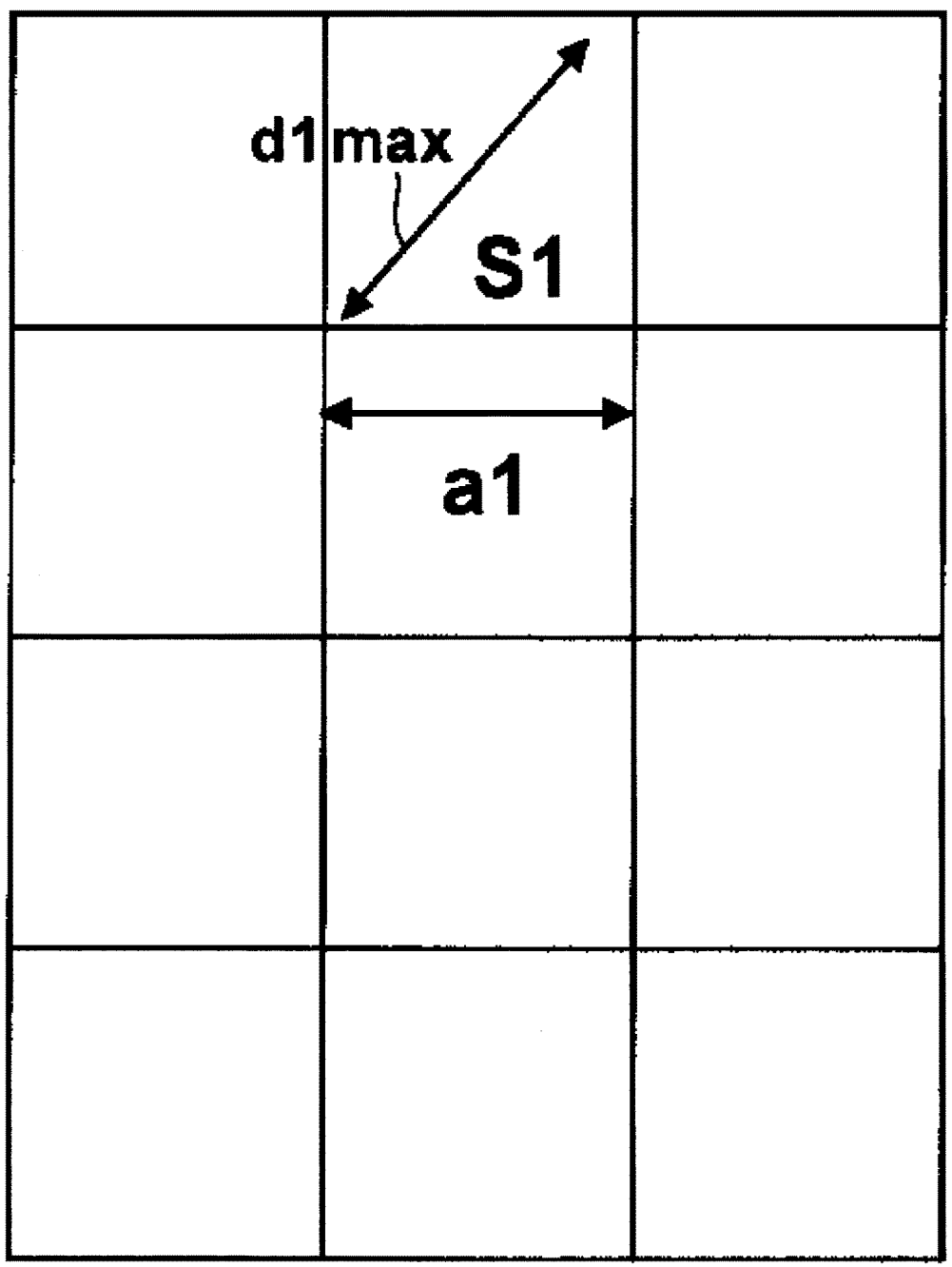
FIG. 8A is a diagram schematically showing a specific example of a shape and array of pixels that detect radiation.
Figure 8B:
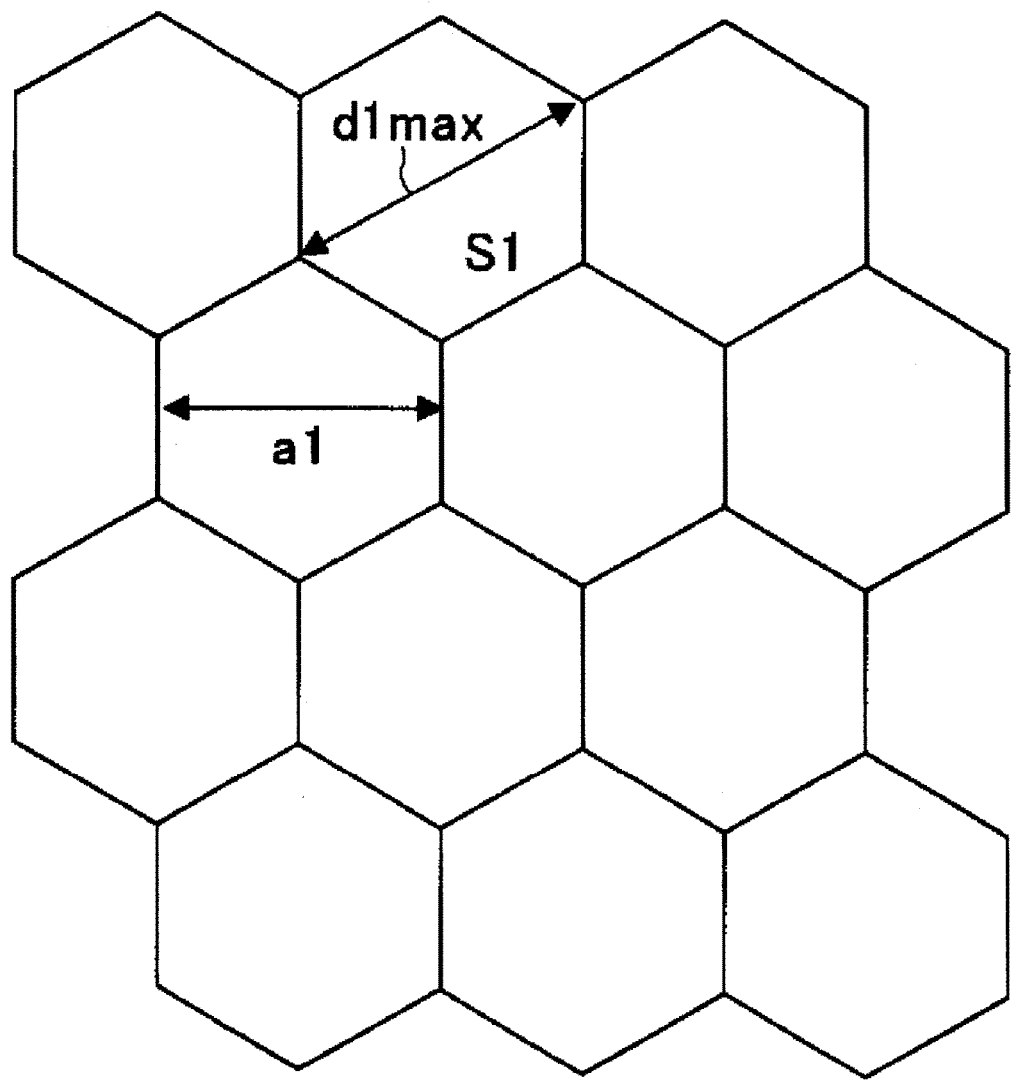
FIG. 8B is a diagram schematically showing a specific example of a shape and array of pixels that detect radiation.

At any rate, in a regular hexagonal state in which the hexagonal shaped pixels are not flattened at all, in (1) of FIG. 5, an array pitch PP1(x) of the pixels in the horizontal direction is shorter than an array pitch PP1(y) of the pixels in the vertical direction. Consequently, a high resolution is ensured in the horizontal direction. By using the second flattening method to flatten the hexagonal shaped pixels in such a way that the diagonal length d1(y) in the vertical direction becomes shorter while keeping this resolution in the horizontal direction ensured, not only the resolution in the horizontal direction but also the resolution in the vertical direction can be ensured. In the case of using these pixels in the radiation detection element 10, the pixels may also rotated 90 degrees from the state shown and used.

Each pixel 20 is configured to include a sensor portion 103 that receives the applied radiation and generates a charge, a charge storing capacitor 108 that stores the charge generated by the sensor portion 103, and a TFT switch 109 for reading out the charge stored in the charge storing capacitor 108.

Further, in the radiation detection element 10, scan lines 101 are disposed one line each for each pixel column with respect to the horizontal direction (hereinafter also called a scan line direction) of the pixels 20. The scan lines 101 are connected to the TFT switches 109 disposed in the pixels 20 of the pixel columns in the scan line direction, and control signals that switch the TFT switches 109 on and off flow through the scan lines 101.

Further, in the radiation detection element 10, signal lines 107 are disposed, in such a way as to snake around the pixels 20, one line each for each pixel column with respect to the vertical direction (hereinafter also called a signal line direction) of the pixels 20. The signal lines 107 are connected to the TFT switches 109 of the pixels 20, and the charges stored in the charge storing capacitors 108 flow through the signal lines 107 in accordance with the switching state of the TFT switches 109.

In the radiation detection element 10 according to the present exemplary embodiment, plural amplifier ICs 105 that detect the electrical signals flowing out to the signal lines 107 are disposed on one end side in the signal line direction. The signal lines 107 are connected to the amplifier ICs 105 every predetermined number of lines.

Further, in the radiation detection element 10 according to the present exemplary embodiment, plural gate ICs 104 that output the control signals for switching the TFTs 109 ON/OFF to the scan lines 101 are disposed on one end side in the scan line direction. The scan lines 101 are connected to the gate ICs 104, and the scan lines 101 are connected to different gate ICs 104 every predetermined number of lines. In FIG. 2, the amplifier ICs 105 and the gate ICs 104 are abbreviated to on each and shown.

The amplifier ICs 105 have, for each signal line 107, built-in amplifier circuits that amplify the input electrical signals. The amplifier ICs 105 amplify, with the amplifier circuits, and detect the electrical signals input from the signal lines 107, whereby the amplifier ICs 105 detect the charge quantity stored in each charge storing capacitor 108 as information of each pixel configuring the image.

A signal processing device 106 is connected to the amplifier ICs 105 and the gate ICs 104. The signal processing device 106 performs predetermined processing such as noise removal on the electrical signals detected in the amplifier ICs 105. In addition, the signal processing device 106 outputs control signals indicating the timings of signal detection to the amplifier ICs 105 and outputs control signals indicating the timings of the output of the scan signals to the gate ICs 104.

Figure 4:
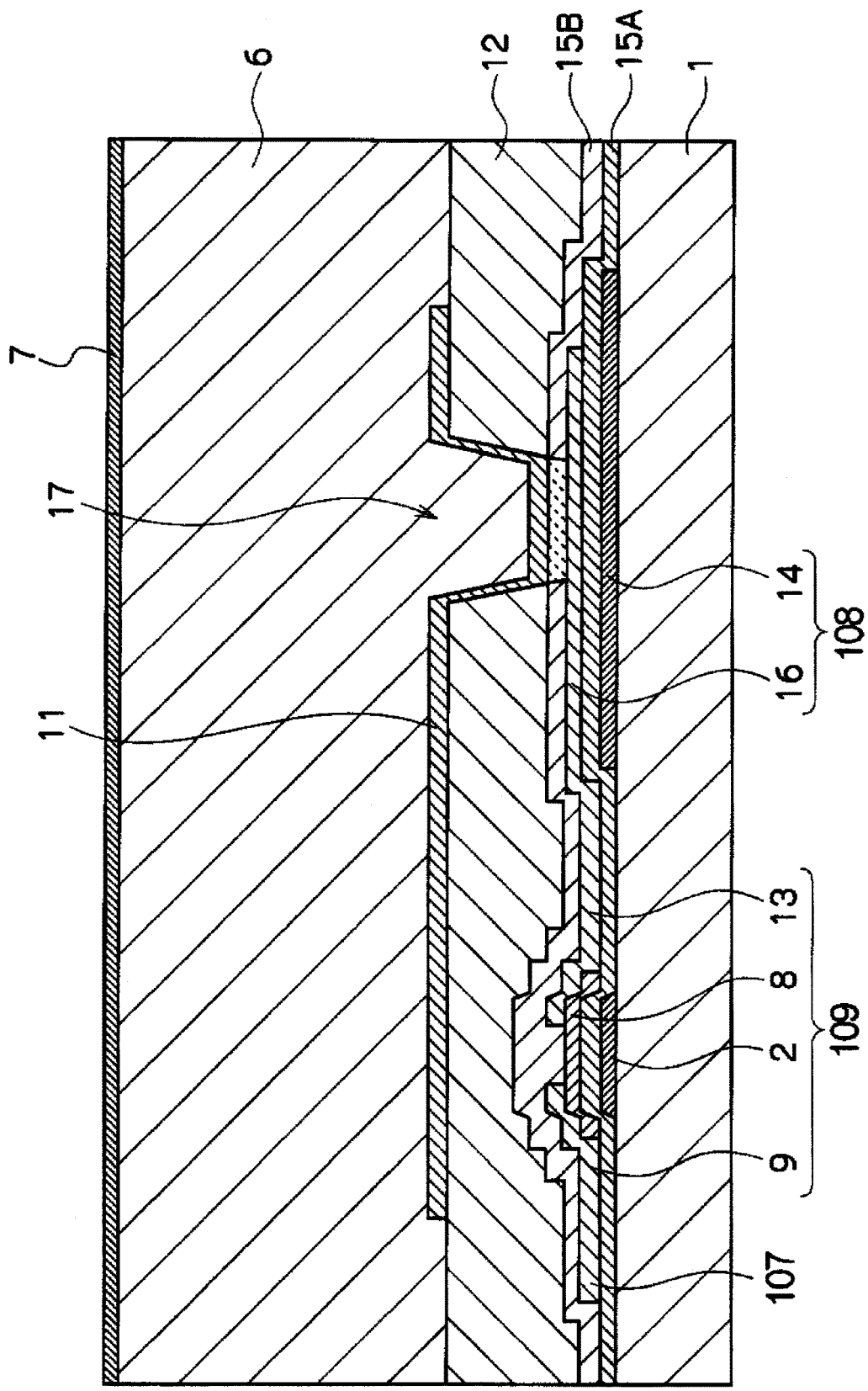
FIG. 4 is a cross-sectional view showing the structure of the radiation detection element according to the exemplary embodiment.

FIG. 4 is a cross-sectional view showing the structure of the radiation detection element 10.

As shown in FIG. 4, the radiation detection element 10 comprises an insulating substrate 1 on which the scan lines 101, storage capacitor lower electrodes 14, and gate electrodes 2 are formed. The scan lines 101 are disposed, in such a way as to circumnavigate between the pixel columns and around the pixels 20, one line each for each pixel column with respect to the scan line direction of the pixels 20. The scan lines 101 are connected to the gate electrodes 2 formed in each pixel 20 of the pixel columns on the upper side and are connected to the storage capacitor lower electrodes 14 formed in each pixel 20 of the pixel columns on the lower side. The wiring layers in which the scan lines 101, the storage capacitor lower electrodes 14, and the gate electrodes 2 are formed (hereinafter these wiring layers will also be called "first signal line layers") are formed using Al or Cu or a laminate film comprising mainly Al or Cu. However, the material of the first signal line layers is not limited to these.

An insulating film 15A is formed on the entire surfaces of the first signal line layers, and the sites positioned on the gate electrodes 2 act as gate insulating films in the TFT switches 109. The insulating film 15A comprises $SiN_x$, for example, and is formed by chemical vapor deposition (CVD) film formation, for example.

Semiconductor active layers 8 are formed like islands over the gate electrodes 2 on the insulating film 15A. The semiconductor active layers 8 are channel portions of the TFT switches 109 and comprise amorphous silicon films, for example.

Source electrodes 9 and drain electrodes 13 are formed on these layers. The signal lines 107 are formed in the wiring layers in which the source electrodes 9 and the drain electrodes 13 are formed, and storage capacitor upper electrodes 16 are formed in positions on the insulating film 15A corresponding to the storage capacitor lower electrodes 14. The drain electrodes 13 are connected to the storage capacitor upper electrodes 16. The signal lines 107 are connected to the source electrodes 9 formed in each pixel 20. The wiring layers in which the source electrodes 9, the drain electrodes 13, the signal lines 107, and the storage capacitor upper electrodes 16 are formed (hereinafter these wiring layers will also be called "second signal line layers") are formed using Al or Cu or a laminate film comprising mainly Al or Cu. However, the material of the second signal line layers is not limited to these. Impurity-added semiconductor layers (not shown) resulting from impurity-added amorphous silicon or the like are formed between the source electrodes 9 and the semiconductor active layers 8 and between the drain electrodes 13 and the semiconductor active layers 8. The TFT switches 109 for switching are configured by these. In the TFT switches 109, the source electrodes 9 and the drain electrodes 13 become reversed because of the polarity of the charges collected and stored by the later-described lower electrodes 11.

Here, as described above, in a case where regions in which shapes having the same area and the same shape including the lower electrodes 11 are arranged in a honeycomb pattern and divided are defined as single pixels of the hexagonal shaped pixels 20, the lower electrodes 11 are disposed inside the shape of the hexagonal shaped pixels 20. Consequently, it is preferred that the lower electrodes 11 be formed in the same hexagonal shape as the hexagonal shaped pixels 20, so that the lower electrodes 11 can more efficiently collect the signal charges generated by the electromagnetic waves, and that the lower electrodes 11 be arranged in a honeycomb pattern. However, as long as the shape of the lower electrodes 11 fits inside the shape of the hexagonal shaped pixels 20, the shape of the lower electrodes 11 is not limited to this, and the lower electrodes 11 may be formed in any shape, such as a substantial hexagon with rounded corners, a tetragon, a circle, or an octagon.

Covering these second signal line layers, a TFT protective film layer 15B is formed on substantially the entire surface (substantially the entire region) of the region on the substrate 1 in which the pixels are disposed. The TFT protective film layer 15B comprises $SiN_x$, for example, and is formed by CVD film formation, for example.

An applied interlayer insulating film 12 is formed on the TFT protective film layer 15B. The interlayer insulating film 12 is formed in a film thickness of 1 to 4 µm by a low-permittivity (relative permittivity $\varepsilon_r$=2 to 4) photosensitive organic material (e.g., a positive-type photosensitive acrylic resin: a material obtained by mixing a naphthoquinone diazide positive-type photosensitizer together with a base polymer comprising a copolymer of methacrylic acid and glycidyl methacrylate).

In the radiation detection element 10 according to the present exemplary embodiment, the capacitance between the metals disposed above and below the interlayer insulating film 12 is kept low by the interlayer insulating film 12. Further, generally this material also has a function as a smoothing film and also has the effect of smoothing out unevenness in the layer below. In the radiation detection element 10 according to the present exemplary embodiment, contact holes 17 are formed in the interlayer insulating film 12 and the TFT protective film layer 15B in positions opposing the storage capacitor upper electrodes 16.

On the interlayer insulating film 12, the lower electrodes 11 of the sensor portions 103 are formed for each pixel 20 in such a way as to fill the contact holes 17 and cover the pixel region. The lower electrodes 11 comprise an amorphous transparent conductive oxide film (ITO) and are connected to the storage capacitor upper electrodes 16 via the contact holes 17. Thus, the lower electrodes 11 and the TFT switches 109 are electrically interconnected via the storage capacitor upper electrodes 16.

A semiconductor layer 6 is uniformly formed on the lower electrodes 11 on substantially the entire surface of the pixel region of the substrate 1 in which the pixels 20 are formed. The semiconductor layer 6 generates charges (electrons-holes) inside when radiation such as X-rays are irradiated. That is, the semiconductor layer 6 is conductive and is for converting image information resulting from X-rays into charge information. Further, the semiconductor layer 6 comprises, for example, amorphous selenium (a-Se) whose main component is selenium. Here, "main component" means having a content percentage equal to or greater than 50%.

An upper electrode 7 is formed on the semiconductor layer 6. The upper electrode 7 is connected to a bias power source (not shown), and a bias voltage is supplied from the bias power source to the upper electrode 7.

Next, the operating principle of the radiation detector 42 according to the present exemplary embodiment will be described.

When X-rays are applied to the semiconductor layer 6 in a state in which the bias voltage has been applied between the upper electrode 7 and the storage capacitor lower electrodes 14, charges (electron-hole pairs) are generated inside the semiconductor layer 6.

The semiconductor layer 6 and the charge storing capacitors 108 have a structure in which they are electrically interconnected in series. For this reason, the electrons generated inside the semiconductor layer 6 migrate to the positive (+) electrode side and the holes migrate to the negative (−) electrode side. At the time of image detection, OFF signals (0 V) are output from the gate ICs 104 to all the scan lines 101, and a negative bias is applied to the gate electrodes 2 of the TFT switches 109. Because of this, each TFT switch 109 is held in an OFF state. As a result, the electrons generated inside the semiconductor layer 6 are collected by the lower electrodes 11 and stored in the charge storing capacitors 108.

At the time of image read-out, ON signals are sequentially output one line at a time from the gate ICs 104 to each scan line 101, and the ON signals (+10 to 20 V) are sequentially applied via the scan lines 101 to the gate electrodes of the TFT switches 109. Because of this, the TFT switches 109 of each pixel 20 of each pixel column in the scan line direction are sequentially switched ON one column at a time, and electrical signals corresponding to the charge quantities stored in the charge storage capacitors 108 of each pixel 20 flow out to the signal lines 107 one column at a time.

The amplifier ICs 105 detect, as information (hereinafter, "pixel information") of the pixels configuring the image, the charge quantities stored in the charge storing capacitors 108 of each sensor portion 103 on the basis of the electrical signals flowing to each signal line 107. Because of this, image data representing the image represented by the X-rays applied to the radiation detection element 10 can be obtained.

The image data obtained by the radiation detection element 10 according to the present exemplary embodiment become image data representing an image in which the pixels are arrayed in a honeycomb pattern. Meanwhile, many output devices such as printers and monitors (in the present exemplary embodiment, the display device 80) are configured with the assumption that they will handle images in which the pixels are arrayed in a square grid pattern. For this reason, in the present exemplary embodiment, the image processing apparatus 50 performs pixel density conversion by performing interpolation processing on the image data representing the detected radiographic image.

FIG. 5 is a schematic diagram schematically showing the content of the pixel density conversion processing.

As was described using FIG. 2 and FIG. 3, the hexagonal shaped pixels are arranged in a honeycomb pattern, so the radiographic image detected by the radiation detection element 10 becomes an image in which the pixels are arrayed in a honeycomb pattern as shown in (1) of FIG. 5. The black points drawn inside the pixels are centers of gravity of the pixels.

The image data representing the radiographic image are converted into image data representing an image in which the plural pixels are arranged in a square grid pattern as shown in (2) of FIG. 5. At this time, the image data are converted in such a way that a surface area S2 of the square grid of the image after the conversion becomes equal to or less than an surface area S1 of the hexagonal shaped pixels before conversion. For the interpolation processing performed in the pixel density conversion, a well-known interpolation process, such as the nearest neighbor algorithm, linear interpolation, or bi-cubic interpolation, can be employed. Further, for example, the image processing apparatus 50 may also be configured to perform the pixel density conversion method described in JP-A No. 2000-244733.

Hereinafter, the image data representing the image in which the pixels are arranged in a honeycomb pattern before the pixel density conversion will be called first image data, and the image data representing the image in which the plural pixels are arranged in a square grid pattern after the pixel density conversion will be called second image data.

In the pixel density conversion, it is preferred that the hexagonal shaped pixels configuring the radiation detection element 10 be formed such that the high resolution across all directions obtained by the radiation detection element 10 does not become wasted (in such a way that the detected signals do not become wasted) and such that the resolution after the pixel density conversion does not become too high compared to the resolution of the radiation detection element, so that the size of the second image data after the conversion does not increase needlessly and processing speed does not drop.

Therefore, in the present exemplary embodiment, the size of the square grid after the pixel density conversion may be adjusted such that the relationship between the hexagonal shaped pixels configuring the radiation detection element 10 and the square grid after the pixel density conversion satisfies Formula (1) below, or the size of the square grid after the pixel density conversion may be adjusted and the hexagonal shaped pixels may be formed in such a way as to satisfy Formula (1) below.

$$\sqrt{S1} \leq d2\max \leq d1\max \quad (1)$$

Here, d2max denotes the length of the diagonals (diagonal length) of the square grid of the second image data after the pixel density conversion. Further, d1max denotes the length of the longest diagonal (hereinafter also called the maximum diagonal length) among the diagonals of the hexagonal shaped pixels before the pixel density conversion. Moreover, S1 denotes the surface area of the hexagonal shaped pixels.

Formula (1) will be described in detail below.

First, the condition of the latter half "d2max≤d1max" of Formula (1) means that the maximum diagonal length of the hexagonal shaped pixels before the pixel density conversion is equal to or greater than the diagonal length of the square grid after the pixel density conversion. By satisfying this condition, the resolution after the conversion becomes equal to or greater than the resolution before the conversion across all direction, and the signals of the pixels detected by the radiation detection element 10 can be prevented from ending up being thrown out (wasted).

Next, the condition of the former half "√(S1)≤d2max" of Formula (1) means that the diagonal length of the square grid after the pixel density conversion is equal to or greater than the length of one side of a square grid having a surface area equal to the surface area S1 of the hexagonal shaped pixels before the pixel density conversion (which is also the array pitch of the pixels in the horizontal direction and the vertical direction). Hereinafter, "√(S1)" will also be called PP0.

Here, d2max denotes the array pitch (maximum pitch) in the direction in which the resolution becomes the lowest among all directions in the pixel array after the conversion. Further, PP0 denotes the array pitch (minimum pitch) in the direction in which the resolution becomes the highest in a square grid having the same area as the hexagonal shaped pixels before the conversion in the radiation detection element. The present exemplary embodiment uses hexagonal shaped pixels instead of square-shaped pixels to detect the radiographic image and performs pixel density conversion, so that a sufficient sensitivity is obtained with the resolution one eventually wants to obtain for the place one originally wants to detect with square-shaped pixels. Consequently, it is not necessary to make the resolution after the pixel density conversion higher than the resolution of the square grid one originally wants to obtain. That is, it is not necessary to make the maximum pitch d2max of the square grid after the pixel density conversion smaller than the minimum pitch PP0 of a square grid having a surface area that is the same as the surface area S1 of the hexagonal shaped pixels used in order to obtain the resolution one originally wants to obtain. Even if d2max is made smaller than PP0, doing so would only amount to the size of the second image data after the conversion increasingly needlessly, bringing about a drop in processing speed.

Consequently, by satisfying the condition of the former half of Formula (1), the present exemplary embodiment may prevent the size of the second image data after the conversion from becoming too large and may prevent a drop in processing speed.

Here, specific examples will be provided to verify, with reference to FIG. 6, whether or not Formula (1) is satisfied.

First, in the example shown in (1) of FIG. 6, the shape of the regular hexagonal pixels before the pixel density conversion is defined as follows (see also (1) of FIG. 5).

surface area S1=4,489.5 μm$^2$
horizontal direction pixel array pitch PP1(x)=72 μm
maximum diagonal length d1max=83.1 μm A square whose surface area is equal to the surface area S1 of these regular hexagonal shaped pixels is expressed by the numerical values below.

surface area S0=S1=4,489.5 μm$^2$
length of one side PP0=√(S1)=67.0 μm Additionally, in a case where the array pitch of the pixels after the pixel density conversion (=the length of one side of the square grid) PP2 is 50 μm, the surface area S2 and the diagonal length d2max of those pixels are as follows (see also (2) of FIG. 5).

surface area S2=2,500 μm
diagonal length d2max=70.7 μm

In this case, the former half "√(S1)≤d2max" of Formula (1) is satisfied because d2max=70.7 μm and PP0=√(S1) =67.0 μm.

Further, the latter half "d2max≤d1max" of Formula (1) is satisfied because d1max=83.1 μm and d2max=70.7 μm.

Next, the value of PP2 will be changed and suitable sizes of the square grid after the pixel density conversion will be found in a case where the maximum diagonal length of the regular hexagonal pixels is such that d1max=80.8 μm.

As shown in (2) of FIG. 6, PP2 is changed in intervals of 5 μm from 65 μm to 45 μm and whether or not Formula (1)

is satisfied is verified. As shown in (2) of FIG. 6, the cases that satisfy the condition of the former half "$\sqrt{(S1)} \leq d2max$" of Formula (1) are the cases where PP2 is 65 μm, 60 μm, 55 μm, and 50 μm, and in the case where PP2 is 45 μm, the condition of the former half is not satisfied.

Meanwhile, the cases that satisfy the condition of the latter half "$d2max \leq d1max$" of Formula (1) are the cases where PP2 is 55 μm, 50 μm, and 45 μm, and in the cases where PP2 is 65 μm and 60 μm, the condition of the latter half is not satisfied.

Consequently, the cases that satisfy both the former half and the latter half of Formula (1) are the cases where PP2 is 55 μm and 50 μm. In the case of detecting a radiographic image using a radiation detection element in which regular hexagonal shaped pixels where PP1(x) is 70 μm are arranged in a honeycomb pattern, it is good for the array pitch (the length of one side) PP2 of the square-shaped pixels after the pixel density conversion to be 55 μm or 50 μm.

Further, the hexagonal shaped pixels may also be formed in such a way that the relationship between the hexagonal shaped pixels configuring the radiation detection element 10 and the square grid after the pixel density conversion satisfies Formula (2) below. Further, the size of the square grid at the time of the pixel density conversion may also be adjusted in such a way as to satisfy Formula (2).

$$d2max \leq d1max \leq \sqrt{(2 \times S1)} \quad \text{Formula (2)}$$

Formula (2) will be described in detail below.

First, the condition of the former half "$d2max \leq d1max$" of Formula (2) is the same as the latter half of Formula (1), and by satisfying this condition, the resolution after the conversion becomes equal to or greater than the resolution before the conversion across all directions, Consequently, the radiation detection element 10 of the present exemplary embodiment can prevent the signals of the pixels it has detected from ending up being thrown out (wasted).

Next, the condition of the latter half "$d1max \leq \sqrt{(2 \times S1)}$" of Formula (2) means that the maximum diagonal length of the hexagonal shaped pixels before the pixel density conversion is equal to or less than the diagonal length of a square having an surface area that is equal to the surface area S1 of those hexagonal shaped pixels. Hereinafter, "$\sqrt{(2 \times S1)}$" will also be called d0max.

Here, d1max denotes the array pitch (maximum pitch) in the direction in which the resolution becomes the lowest among all directions in the pixel array before the conversion. Originally, resolution is increased by using hexagonal shaped pixels rather than square-shaped pixels, but when d1max becomes larger than the diagonal length d0max of a square having the same surface area S1 as the hexagonal shaped pixels, the resolution becomes lower than when using square-shaped pixels whose area is the same, so the effect of the hexagonal shape is not sufficiently obtained.

Consequently, the present exemplary embodiment can exhibit the advantage of sensitivity and can also improve the resolution by forming the hexagonal shaped pixels in such a way as to satisfy the condition of the latter half. For example, even in the case of flattening the hexagonal shape to raise the resolution, by forming the pixels of the radiation detection element 10 with a flattening ratio that satisfies this condition, the present exemplary embodiment can ensure a high resolution in all directions.

Here, specific examples will be provided to verify, with reference to FIG. 7, whether or not Formula (2) is satisfied.

First, in (1) of FIG. 7, the shape of the regular hexagonal pixels before the pixel density conversion is defined as follows (see also (1) of FIG. 5).

surface area S1=4,871.4 μm²
horizontal direction pixel array pitch PP1(x)=75 μm
maximum diagonal length d1max=86.6 μm A square whose surface area is equal to the surface area S1 of these regular hexagonal shaped pixels is expressed by the numerical values below.

surface area S0=S1=4,871.4 μm²
length of one side PP0=$\sqrt{(S1)}$=69.8 μm
diagonal length d0max=$\sqrt{(2 \times S1)}$=98.7 μm Additionally, in a case where the pixel array pitch after the pixel density conversion (=the length of one side of the square grid) PP2 is 50 μm, the surface area S2 and the diagonal length d2max of those pixels are as follows (see also (2) of FIG. 5).

surface area S2=2,500 μm²
diagonal length d2max=70.7 μm

In this case, the former half "$d2max \leq d1max$" of Formula (2) is satisfied because d1max=86.6 μm and d2max=70.7 μm.

Further, the latter half "$d1max \leq d0max$" of Formula (2) is satisfied because d1 max=86.6 μm and d0max=98.7 μm.

Next, flattened hexagonal shaped pixels will be taken as an example and described. Here, "flattened" means a state in which any one diagonal of the diagonals passing through the center of the pixel is shorter than the other two diagonals and that the lengths of those other two diagonals is equal. Specific examples of the relationship between Formula (2) and the flattening ratio of the hexagonal pixels will be described below focusing on the condition of the latter half of Formula (2).

In the table in (2) of FIG. 7, d1(y) is the length of one diagonal (here, the diagonal length in the vertical direction in (1) of FIG. 5) of the diagonals passing through the center of the hexagonal shaped pixel. Additionally, when d1(x) denotes the length of the remaining two diagonals (whose lengths are mutually equal), excluding the diagonal in the vertical direction, of the diagonals passing through the center of the hexagonal shaped pixel, the value expressed by d1(y)/d1(x) is the flattening ratio. In a case where the pixels are flattened in such a way that the pixels are crushed in the vertical direction using the aforementioned second flattening method, d1(x)=d1max.

As shown in (2) of FIG. 7, in the case where the flattening ratio is 100%, the condition of the latter half "$d2max \leq d1max$" of Formula (2) is satisfied. In the case where the flattening ratio is 70%, d1max is substantially equal to d0max. Additionally, in the case where the flattening ratio is 63%, d1max greatly exceeds d0max, so the condition of the latter half of Formula (2) is no longer satisfied. This means that it is necessary to make the flattening ratio equal to or greater than about 70% in order to satisfy the condition of the latter half of Formula (2). In this way, a flattening ratio that has a high resolution and can exhibit the advantage of sensitivity is defined by Formula (2).

In the case of flattening the hexagonal shaped pixels, the pixels can be flattened in such a way as to satisfy Formula (3) below. In this case, the resolution improves over that of regular hexagonal shaped pixels.

$$d1max < \sqrt{(8/3\sqrt{3}) \times S1} \quad \text{Formula (3)}$$

Incidentally, the image processing apparatus 50 may perform the interpolation processing when performing the pixel density conversion in such a way as to first perform the interpolation processing in the direction in which the array pitch of the pixels is shorter among the horizontal direction and the vertical direction and thereafter perform the interpolation processing in the other direction. By performing the interpolation processing beginning with the direction in which the distance is short, precision becomes higher than performing the interpolation processing beginning with the opposite direction, and conversion speed also becomes faster.

For example, in a case where the horizontal direction pixel array pitch PP1(x) is shorter than the vertical direction pixel array pitch PP1(y), the image processing apparatus 50 first performs the interpolation processing in the horizontal direction and then performs the interpolation processing in the vertical direction after the interpolation processing in the horizontal direction. Further, in a case where, conversely, the vertical direction pixel array pitch PP1(y) is shorter than the horizontal direction pixel array pitch PP1(x), the image processing apparatus 50 first performs the interpolation processing in the vertical direction and then performs the interpolation processing in the horizontal direction after the interpolation process in the vertical direction.

Because of this, the information detected by the radiation detection element 10 of the present exemplary embodiment can be sufficiently utilized.

The state of the arrangement of the gate ICs 104 and the amplifier ICs 105 of the above-described exemplary embodiment, the state of the connection of the signal lines 107, and the state of the connection of the scan lines 101 are examples and are not limited to the above-described exemplary embodiment.

Figure 9:
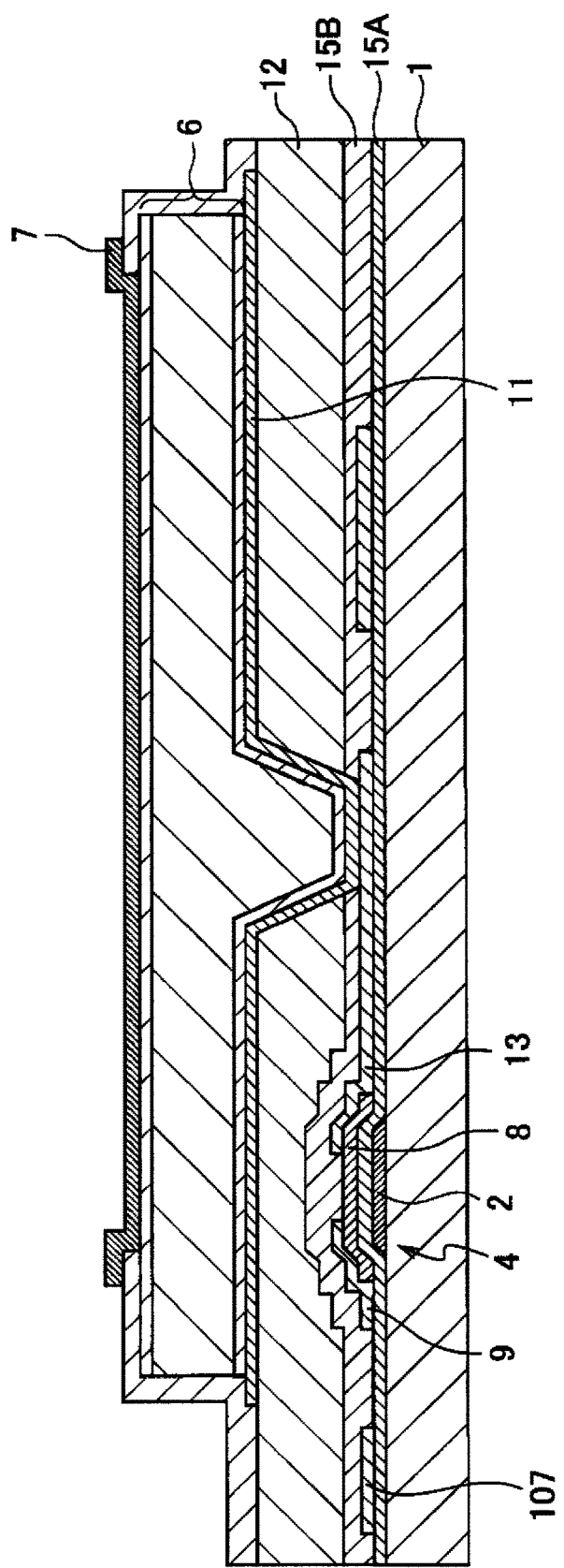
FIG. 9 is a cross-sectional view showing the structure of the radiation detection element according to the exemplary embodiment.

Further, in the above-described exemplary embodiment, a case where the present invention was applied to the direction conversion type radiation detection element 10 was described, but the present invention may also be applied to an indirect-conversion-type radiation detection element 10. FIG. 9 shows an example of the indirect-conversion-type radiation detection element 10. In the case of the indirect-conversion-type, a scintillator layer (not shown; for example, CsI:Tl, GOS(Gd$_2$O$_2$S:Tb) that first converts the radiation into light is disposed in the detection region 40. Further, in the indirect-conversion-type radiation detection element 10, under the scintillator layer, the semiconductor layer 6, which converts into charges the light into which the radiation has been converted, and the lower electrodes 11, which collect the charges, are disposed in each pixel just like the photoelectric conversion layer 6 and the lower electrodes 11 in the direct-conversion-type shown in FIG. 4. Moreover, the indirection conversion type radiation detection element 10 is equipped with switch elements 4 that read out the charges collected by the lower electrodes 11. For the other configurations of the indirect-conversion-type radiation detection element 10, it suffices to configure them by appropriately substituting the configurations of the direct-conversion-type shown in FIGS. 1, 2, 3, and 4.

In the case of the indirect-conversion-type, the semiconductor layer 6 that converts the light into charges may be divided per pixel 20, and the upper electrode 7 that supplies the bias to the semiconductor layer 6 may also be divided per pixel 20. In a case where the above-described exemplary embodiment is applied to the indirect-conversion-type radiation detection element 10, the pixels 20 are such that hexagonal regions in which shapes having the same area and the same shape including at least one of the lower electrodes 11, the semiconductor layer 6, the upper electrode 7, and the switch elements 4 are arranged (that is, plane tessellation: gapless tiling) in a honeycomb pattern and divided are defined as single pixels. However, the way of defining the pixels 20 is not limited to this, and the substantially hexagonal regions formed by the signal lines 107 may also be defined as single pixels.

Further, in the above-described exemplary embodiment, an example where the function of a pixel density conversion section that performs pixel density conversion was disposed in the image processing apparatus 50 and where the image processing apparatus 50 was configured as a device independent of the imaging device 41 including the radiation detection element 10 was described. However, the present invention is not limited to this. For example, the present invention may also have a configuration where an image density conversion section or the section of the image processing apparatus 50 having the image processing function of performing the pixel density conversion is disposed in the radiation detector 42. Further, as another example, the present invention may also be a system in which the imaging device 41 and the image processing apparatus 50 that performs the pixel density conversion are interconnected via a network.

Further, in the above-described exemplary embodiment, a case where the present invention was applied to the radiation detector 42 that detects an image by detecting X-rays as the radiation serving as the detection target was described. However, the present invention is not limited to this. For example, the radiation serving as the detection target may also be any of visible light, ultraviolet rays, infrared rays, α rays, or γ rays.

Further, in the above-described exemplary embodiment, a case where the radiation detection element 10 was equipped with the charge storing capacitors 108 for each pixel 20 was described. However, for example, there are also cases where the lower electrodes 11 have a capacity that can sufficiently store the charges and cases where the charge storing capacitors 108 are not formed for each pixel 20.

In addition, the configuration of the radiographic imaging system 100, the configuration of the radiation detection element 10 described in the above-described exemplary embodiment, and so forth are examples and can be appropriately changed in the scope of the gist of the present invention.

The disclosure of Japanese Patent Application No. 2011-177363 is incorporated in its entirety by reference in the present specification.

All publications, patent applications, and technical standards mentioned in the present specification are incorporated by reference in the present specification to the same extent as if each individual publication, patent application, or technical standard was specifically and individually indicated to be incorporated by reference.

What is claimed is:
1. A radiographic imaging device comprising:
a radiation detection element including a plurality of same sized hexagonal shaped pixels that detect radiation and are arrayed in a honeycomb pattern; and
a pixel density conversion section that performs interpolation processing such that first image data obtained from the radiation detection element is converted into second image data representing an image in which plural pixels are arrayed in a square grid pattern,
wherein, in the radiographic imaging device, the following expression is satisfied,

$$\sqrt{S1} \le d2\max \le d1\max < \sqrt{(2 \times S1)}$$

wherein d1max denotes the length of the longest diagonal of the hexagonal shaped pixels, S1 denotes the surface area of the hexagonal shaped pixels, and d2max denotes the length of the diagonals of the square grid of the second image data.

2. The radiographic imaging device of claim 1, wherein the direction of one axis of the diagonals of the hexagonal shaped pixels coincides with the direction of one axis of the square grid, and the hexagonal shape is symmetrical with respect to the one axis of the diagonals.

3. The radiographic imaging device of claim 1, wherein the hexagonal shaped pixels are formed to have a regular hexagonal shape.

4. The radiographic imaging device of claim 1, wherein the pixel density conversion section performs interpolation processing first in the direction out of a horizontal direction and a vertical direction in the first image data that has a shorter pixel array pitch, and then performs the interpolation processing in the other direction.

5. The radiographic imaging device of claim 1, further comprising:
a radiation source that irradiates radiation; and
an image output device that outputs an image on the basis of the second image data.

6. A radiographic imaging method comprising:
detecting first image data using a radiation detection element that includes a plurality of same sized hexagonal shaped pixels that detect radiation and are arrayed in a honeycomb pattern; and
performing interpolation processing such that the first image data is converted into second image data representing an image of a plurality of pixels arrayed in a square grid pattern,
wherein, in the radiographic imaging method, the following expression is satisfied, $$\sqrt{S1} \leq d2\max \leq d1\max < \sqrt{(2 \times S1)}$$

wherein d1max denotes the length of the longest diagonal of the hexagonal shaped pixels, S1 denotes the surface area of the hexagonal shaped pixels, and d2max denotes the length of the diagonals of the square grid of the second image data.

7. The radiographic imaging method of claim 6, wherein the direction of one axis of the diagonals of the hexagonal shaped pixels coincides with the direction of one axis of the square grid, and the hexagonal shape is symmetrical with respect to the one axis of the diagonals.

8. The radiographic imaging method of claim 6, wherein the hexagonal shaped pixels have a regular hexagonal shape.

9. The radiographic imaging method of claim 6, wherein the interpolation processing is first performed in the direction out of a horizontal direction and a vertical direction in the first image data that has a shorter pixel array pitch, and then performs the interpolation processing in the other direction.

10. The radiographic imaging method of claim 6, further comprising outputting an image based on the second image data.

11. The radiographic imaging device of claim 1, wherein the hexagonal shaped pixels have flattened hexagonal shape in which one diagonal of diagonals passing through a center is shorter than other two diagonals and lengths of the other two diagonals is equal,
wherein flattening ratio of the flattened hexagonal shape is equal to or more than 70% and is less than 100%, and
wherein, $d2\max \leq d1\max < \sqrt{(2 \times S1)}$ is also satisfied.

12. The radiographic imaging method of claim 6, wherein the hexagonal shaped pixels have flattened hexagonal shape in which one diagonal of diagonals passing through a center is shorter than other two diagonals and lengths of the other two diagonals is equal,
wherein flattening ratio of the flattened hexagonal shape is equal to or more than 70% and is less than 100%, and
wherein, $d2\max \leq d1\max < \sqrt{(2 \times S1)}$ is also satisfied.

* * * * *